(12) United States Patent
Fecant et al.

(10) Patent No.: US 8,476,186 B2
(45) Date of Patent: Jul. 2, 2013

(54) SELECTIVE HYDROGENATION CATALYST AND PROCESS FOR ITS PREPARATION

(75) Inventors: Antoine Fecant, Brignais (FR); Lars Fischer, Vienne (FR); Bernadette Rebours, Lyons (FR); Renaud Revel, Serpaize (FR); Cecile Thomazeau, Brignais (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 771 days.

(21) Appl. No.: 12/488,280

(22) Filed: Jun. 19, 2009

(65) Prior Publication Data

US 2009/0318738 A1    Dec. 24, 2009

(30) Foreign Application Priority Data

Jun. 20, 2008    (FR) ..................... 08 03482

(51) Int. Cl.
B01J 23/44        (2006.01)
C07C 5/05         (2006.01)

(52) U.S. Cl.
USPC ........... 502/333; 502/325; 502/332; 502/439; 585/258; 585/259; 585/260

(58) Field of Classification Search
USPC .......... 502/300, 325, 332, 333, 439; 585/250, 585/258, 259, 260
See application file for complete search history.

(56) References Cited

U.S. PATENT DOCUMENTS

| | | | | |
|---|---|---|---|---|
| 3,222,129 A * | 12/1965 | Osment et al. | | 423/628 |
| 3,223,483 A * | 12/1965 | Osment | | 423/131 |
| 4,051,072 A * | 9/1977 | Bedford et al. | | 502/323 |
| 4,120,942 A * | 10/1978 | Spitzer et al. | | 423/626 |
| 4,230,897 A * | 10/1980 | Cosyns et al. | | 585/260 |
| 5,866,735 A * | 2/1999 | Cheung et al. | | 585/273 |
| 5,972,820 A * | 10/1999 | Kharas et al. | | 501/127 |
| 6,043,187 A | 3/2000 | Harle et al. | | |
| 6,309,537 B1 | 10/2001 | Harle et al. | | |
| 6,403,526 B1 * | 6/2002 | Lussier et al. | | 502/439 |
| 6,437,206 B1 | 8/2002 | Meyer et al. | | |
| 7,125,538 B2 * | 10/2006 | Le Loarer et al. | | 423/625 |
| 2007/0098611 A1 * | 5/2007 | Yang | | 423/213.2 |

FOREIGN PATENT DOCUMENTS

| EP | 0576828 A1 | 1/1994 |
|---|---|---|
| EP | 0576828 W | 1/1994 |
| EP | 1897613 A1 | 3/2008 |
| EP | 1897613 W | 3/2008 |

\* cited by examiner

*Primary Examiner* — In Suk Bullock
*Assistant Examiner* — Bradley Etherton
(74) *Attorney, Agent, or Firm* — Millen, White, Zelano & Branigan, P.C.

(57) ABSTRACT

The invention concerns a catalyst comprising palladium on an oxide of aluminum support. In the calcined state, the oxide of aluminum support has a diffractogram obtained by X ray diffraction comprising peaks which correspond to the following interplanar spacings and relative intensities:

| Interplanar spacings $d\ (10^{-10}\ m)$ $\pm 5 \times 10^{-3}\ d$ | Relative intensities $I/I_0\ (\%)$ |
|---|---|
| 4.54 | 3-10 |
| 2.70-2.75 | 5-25 |
| 2.41 | 35-45 |
| 2.28 | 15-30 |
| 2.10 | 0-10 |
| 1.987 | 30-50 |
| 1.958 | 30-50 |
| 1.642 | 0-5 |
| 1.519 | 10-20 |
| 1.394 | 100 |

13 Claims, No Drawings

SELECTIVE HYDROGENATION CATALYST AND PROCESS FOR ITS PREPARATION

The selective hydrogenation process can transform polyunsaturated compounds in oil cuts by conversion of the most unsaturated compounds into the corresponding alkenes, avoiding total saturation and thus the formation of the corresponding alkanes.

The aim of the invention is to propose a catalyst with improved performances applied to the process for selective hydrogenation of unsaturated hydrocarbon compounds present in hydrocarbon cuts, preferably cuts derived from steam cracking or catalytic cracking.

The groups of the chemical elements mentioned below are given in accordance with the CAS classification (CRC Handbook of Chemistry and Physics, pub. CRC Press, Editor-in-chief D R Lide, 81$^{st}$ edition, 2000-2001). As an example, group VIII in the CAS classification corresponds to metals from columns 8, 9 and 10 of the new IUPAC classification.

PRIOR ART

Selective hydrogenation catalysts are generally based on metals from group VIII of the periodic table of the elements, preferably palladium or nickel. The active phase of the catalysts is in the form of small metal particles deposited on a support which may be a refractory oxide in the form of beads, extrudates, trilobes or in forms having other geometries. The metal content, the possible presence of a second metallic element, the metal particle size and the distribution of the active phase in the support are criteria which are of importance to the activity and selectivity of the catalysts.

The present invention is aimed at obtaining catalysts based on palladium with improved physico-chemical properties and catalytic performances compared with catalysts based on palladium of the prior art.

The catalysts of the invention comprise palladium deposited on an alumina support, said alumina support having a particular crystallographic structure and thus a particular diffractogram obtained by X ray diffraction. This particular property of the support is at the origin of the improvement in the catalytic performance.

Prior art patents have selective hydrogenation catalysts comprising at least one noble metal and a support based on alumina or supports for catalysts of the aluminium oxide type, having particular X ray diffractograms. U.S. Pat. No. 6,437,206 B and EP-0 576 828 can be cited in particular. However, those diffractograms obtained for the supports or catalysts of the prior art differ from those of the present invention in the presence and/or absence and/or intensity of the peaks obtained for given interplanar spacings.

SUMMARY OF THE INVENTION

The invention concerns a catalyst comprising palladium on an oxide of aluminium support. The oxide of aluminium support has, in the calcined state, a diffractogram obtained by X ray diffraction comprising peaks which correspond to the following interplanar spacings and relative intensities:

| Interplanar spacings<br>d ($10^{-10}$ m)<br>$\pm 5 \times 10^{-3}$ d | Relative intensities<br>$I/I_0$ (%) |
| --- | --- |
| 4.54 | 3-10 |
| 2.70-2.75 | 5-25 |
| 2.41 | 35-45 |
| 2.28 | 15-30 |
| 2.10 | 0-10 |
| 1.987 | 30-50 |
| 1.958 | 30-50 |
| 1.642 | 0-5 |
| 1.519 | 10-20 |
| 1.394 | 100 |

DETAILED DESCRIPTION OF THE INVENTION

The aim of the present invention is to obtain catalysts based on palladium having improved physico-chemical and catalytic performances compared with prior art catalysts based on palladium. More precisely, the present invention proposes a process for preparing an alumina support as well as the preparation of a catalyst on said alumina support, and a selective hydrogenation process using said catalyst resulting in improved catalytic performances for said catalyst.

The present invention concerns catalysts comprising palladium on an alumina support. In the calcined state, the alumina support has a diffractogram obtained by X ray diffraction comprising peaks which correspond to the following interplanar spacings and relative intensities:

| Interplanar spacings<br>d ($10^{-10}$ m)<br>$\pm 5 \times 10^{-3}$ d | Relative intensities<br>$I/I_0$ (%) |
| --- | --- |
| 4.54 | 3-10 |
| 2.70-2.75 | 5-25 |
| 2.41 | 35-45 |
| 2.28 | 15-30 |
| 2.10 | 0-10 |
| 1.987 | 30-50 |
| 1.958 | 30-50 |
| 1.642 | 0-5 |
| 1.519 | 10-20 |
| 1.394 | 100 |

Only peaks with a relative intensity of 1% or more are considered.

Throughout the text, the interplanar spacings are given with a relative precision of 0.5%, denoted $\pm 5 \times 10^{-3}$ d.

The diffractogram is characteristic of the specific structure of the support of the catalyst of the invention. The alumina support may include impurities and additives as long as the diffractogram remains as described above. As an example, the support may include inorganic oxides such as oxides of metals from groups IIA, IIIB, IVB, IIB, IIIA, IVA of the CAS classification, preferably silica, titanium dioxide, zirconium dioxide, zinc oxide, magnesium oxide and calcium oxide.

The quantity of cations from columns IIA, IIIB, IVB, IIB, IIIA, IVA is preferably in the range 0.01% to 30% by weight, preferably in the range 0.01% to 10% by weight, more preferably in the range 0.03% to 1.5% by weight. The quantity of one or more metals from group IB may be in the range 1 to 10000 ppm by weight with respect to the support.

The maximum quantity of oxides other than alumina in the support depends on the oxides present. It may be determined by the diffractogram since a change in structure is associated with a change in diffractogram. In general, the quantity of such oxides is less than 50%, preferably less than 30%, more preferably in the range 0.01% to 15% by weight with respect to the mass of the support.

According to the invention, the porous support is advantageously in the form of beads, trilobes, extrudates, pellets, or irregular non-spherical agglomerates the specific form of which may be the result of a crushing step. Highly advantageously, said support is in the form of beads or extrudates. More advantageously, said support is in the form of beads.

The pore volume of the support is generally in the range 0.1 to 2.0 cm$^3$/g, preferably in the range 0.5 to 1.5 cm$^3$/g.

The specific surface area of the porous support is in the range 60 to 210 m$^2$/g, preferably in the range 80 to 180 m$^2$/g, more preferably in the range 100 to 160 m$^2$/g.

The amount of palladium in the catalyst is generally in the range from 0.01% to 2% by weight, more preferably in the range 0.03% to 1% by weight and still more preferably in the range 0.05% to 0.8%.

In addition to the characteristic peaks of the support, the diffractogram of the catalyst in the oxide form may thus have the characteristic peaks of palladium, in the oxide or metal form, or in the form in which it is in combination with other compounds (palladium nitrate, palladium chlorate, palladium formate). The skilled person will refer to ICDD (International Center for Diffraction Data) tables for the positions of these peaks for each of the above named compounds. As an example, the positions of the peaks for palladium oxide (Pd$_O$) are recorded in table 00-041-1107 and the positions of the peaks for metallic palladium (Pd$^0$) are recorded in table 00-046-1043.

In the table below, only peaks with relative intensities I/I$_0$ of more than 10 and with interplanar spacings of more than 1.35 have been recorded. The column "hkl" corresponds to the Miller indices.

| PDF 41-1107 (PdO) | | | PDF 46-1043 (Pd$^0$) | | |
|---|---|---|---|---|---|
| d (Å) | I/I$_0$ | hkl | d (Å) | I/I$_0$ | hkl |
| 2.67 | 22 | 002 | | | |
| 2.65 | 100 | 101 | | | |
| | | | 2.25 | 100 | 111 |
| 2.15 | 14 | 110 | | | |
| | | | 1.945 | 60 | 200 |
| 1.676 | 20 | 112 | | | |
| 1.535 | 15 | 103 | | | |
| 1.523 | 11 | 200 | | | |
| | | | 1.375 | 42 | 220 |

Preparation of Support

In accordance with a first variation, the supports of the invention are alumina agglomerates in the form of beads. In accordance with this first variation, preparation of the support comprises the following steps:

s1) dehydration by flash calcining an aluminium hydroxide or oxyhydroxide, preferably hydrargillite, to obtain an active alumina powder:

Flash calcining is intense and rapid heating which results in severe and sudden dehydration of an aluminium hydroxide (hydrargillite, gibbsite or bayerite) or an aluminium oxyhydroxide (boehmite or diaspore) using a stream of hot gas which can eliminate and entrain evaporated water very rapidly. The temperature is in the range 400° C. to 1200° C., preferably in the range 600° C. to 900° C. and the duration is in the range from a fraction of a second to 5 seconds, preferably in the range 0.1 seconds to 4 seconds. The starting compound which is preferably used is hydrargillite. Experience has shown that this compound is most favorable for producing a final product having the desired properties. Further, it is relatively inexpensive.

In general, the active alumina powder obtained after dehydration of the aluminium hydroxide or oxyhydroxide is ground.

In general, the active alumina powder obtained after dehydration of the aluminium hydroxide or oxyhydroxide is washed with water or an aqueous acid solution.

s2) shaping said active alumina powder to obtain beads with a loose packing density in the range 500 to 1100 kg/m$^3$, preferably in the range 700 to 950 kg/m$^3$, and with a diameter mainly in the range 0.8 to 10 mm, preferably in the range 1 to 5 mm;

Said active alumina powder is generally formed to obtain beads, termed granulation, by using a rotary technique such as a rotary bowl granulator or a rotary drum. This type of process can produce beads with a controlled diameter and pore distribution, these dimensions and distributions generally being created during the agglomeration step. The pores may be created by different means, such as the choice of the granulometry of the alumina powder or the agglomeration of several alumina powders with different granulometries. Another method consists of mixing one or more compounds termed porogens with the alumina powder before or during the agglomeration step; said porogens disappear by heating, thereby creating porosity in the beads. Examples of porogenic compounds which may be used which may be cited include wood flour, wood charcoal, sulphur, tars, plastic materials or emulsions of plastic materials such as polyvinyl chloride, polyvinyl alcohols, naphthalene or the like. The quantity of porogenic compounds added is determined by the desired volume. During forming of said alumina powder, one or more porogenic materials are added thereto which disappear on heating. Said porogenic materials are selected from the group constituted by wood flour, wood charcoal, sulphur, tars, plastic materials or emulsions of plastic materials such as polyvinyl chloride, polyvinyl alcohols and naphthalene.

s3) Heat treatment at a temperature in the range 200° C. to 1200° C., preferably in the range 400° C. to 900° C., of said beads to provide a specific surface area in the range 50 to 420 m$^2$/g.

s4) Hydrothermal treatment of said beads by impregnation with water or an aqueous solution, preferably acidic, then placing in an autoclave at a temperature in the range 100° C. to 300° C., preferably in the range 150° C. to 250° C.

The hydrothermal treatment is generally carried out at a temperature of 100° C. to 300° C., preferably 150° C. to 250° C., for a period of more than 45 minutes, preferably 1 to 24 hours, highly preferably 1.5 to 12 hours. The hydrothermal treatment is generally carried out using an aqueous acid solution comprising one or more mineral and/or organic acids, preferably nitric acid, hydrochloric acid, perchloric acid, sulphuric acid, or weak acids which in solution have a pH of less than 4, such as acetic acid or formic acid. Generally, said aqueous acid solution also includes one or more compounds which can liberate anions capable of combining with aluminium ions, preferably compounds comprising a nitrate ion (such as aluminium nitrate), chloride, sulphate, perchlorate, chloroacetate, trichloroacetate, bromoacetate, dibromoacetate and anions with general formula: R—COO such as formates and acetates.

s5) Calcining the agglomerates obtained at a temperature in the range 500° C. to 820° C., preferably in the range 550° C. to 750° C.

This calcining is generally carried out to obtain a specific surface area for the support in the range 60 to 120 m$^2$/g and to obtain the desired X ray diffractogram.

In accordance with a second variation, the supports of the invention are alumina agglomerates in the form of extruded materials. In this second variation, the preparation of the support comprises the following steps:

s1) Milling and extruding a material based on alumina to form it:

In general, said material based on alumina is dehydrated hydrargillite. The alumina-based material may also generally be derived from the precipitation of boehmite, pseudo-boehmite or bayerite, or a mixture thereof.

When forming said alumina-based material, in general one or more porogenic materials are added thereto which disappear on heating.

Said porogenic materials are selected from the group constituted by wood flour, wood charcoal, sulphur, tars, plastic materials, emulsions of plastic materials, polyvinyl alcohols and naphthalene.

s2) Heat treating at a temperature in the range 200° C. to 1200° C. of the extruded materials obtained, to provide a specific surface area in the range 50 to 420 m$^2$/g;

s3) Hydrothermal treatment of said extrudated materials by impregnating with water or an aqueous solution, preferably acidic, then placing in an autoclave at a temperature in the range 100° C. to 300° C., preferably in the range 150° C. to 250° C.

The hydrothermal treatment is generally carried out at a temperature of 100° C. to 300° C., preferably 150° C. to 250° C., for a period of more than 45 minutes, preferably 1 to 24 hours, highly preferably 1.5 to 12 hours. The hydrothermal treatment is generally carried out using an aqueous acid solution comprising one or more mineral and/or organic acids, preferably nitric acid, hydrochloric acid, perchloric acid, sulphuric acid, or weak acids which in solution have a pH of less than 4, such as acetic acid or formic acid. Generally, said aqueous acid solution also includes one or more compounds which can liberate anions capable of combining with aluminium ions, preferably compounds comprising a nitrate ion (such as aluminium nitrate), chloride, sulphate, perchlorate, chloroacetate, trichloroacetate, bromoacetate, dibromoacetate and anions with general formula: R—COO such as formates and acetates.

s4) calcining the agglomerates obtained at a temperature in the range 500° C. to 820° C., preferably in the range 550° C. to 750° C.

Said calcining is generally carried out in order to obtain a specific surface area of the support in the range 60 to 210 m$^2$/g and to obtain the desired X ray diffractogram.

Preparation of Catalysts

The catalysts are prepared using any method which is known to the skilled person.

c1) Preparation of a Solution Comprising Palladium

The palladium precursor salt is generally selected from the group constituted by palladium chloride, palladium nitrate and palladium sulphate. Highly preferably, the precursor palladium salt is palladium nitrate. The concentration of the aqueous solution of the palladium precursor is adjusted for the desired weight content of the palladium in the catalyst.

Optionally, said palladium precursor solution may be neutralized with a hydroxide selected from the group constituted by alkali hydroxides and alkaline-earth hydroxides to form a colloidal suspension of palladium oxide particles, the pH of said colloidal suspension being in the range 1.0 to 3.5.

c2) Impregnation of the Solution onto the Alumina Support

The alumina support may be impregnated by dry impregnation, in excess or in deficiency, in static or dynamic mode. Impregnation may be carried out in one or more successive impregnation steps.

c3) Drying of Catalyst

The impregnated catalyst is generally dried in order to eliminate all or part of the water introduced during impregnation, preferably at a temperature in the range 50° C. to 250° C., more preferably in the range 70° C. to 200° C. Drying is carried out in air, or in an inert atmosphere (for example nitrogen).

c4) Calcining of Catalyst (Optional)

The catalyst is then calcined, generally in air. The calcining temperature is generally in the range 250° C. to 900° C., preferably in the range from approximately 300° C. to approximately 500° C. The calcining period is generally in the range 0.5 hours to 5 hours.

c5) Activation by Reduction of Catalyst Obtained in Preceding Step

The catalyst is generally reduced. This step is preferably carried out in the presence of a reducing gas, preferably using gaseous hydrogen in situ, i.e. in the reactor where the catalytic transformation is carried out.

Preferably, for catalysts based on palladium, this step is carried out at a temperature in the range 50° C. to 300° C., more preferably in the range 80° C. to 160° C.

In a variation of the catalyst preparation, the catalyst is prepared in a plurality of impregnations.

For catalysts prepared in two impregnation steps, the sequences may be as follows:

impregnation no 1—drying—impregnation no 2—drying—calcining;

impregnation no 1—drying—calcining—impregnation no 2—drying—calcining.

The invention also concerns the catalyst obtained from the catalyst preparation processes described in the present invention.

Characterization of Support

The diagrams of the various supports cited in this document were recorded on a diffractometer (X'PERT'Pro from PANalytical) in Bragg-Brentano geometry, equipped with a copper tube (1.54 Å), a proportional counter and slits with an opening which varied as a function of 2θ. The surface area of the irradiated sample was 10×10 mm; the sampling increment was 0.05°2θ; the time per increment was 5 to 15 s.

After recording, the intensities were corrected and transformed into intensities with a constant irradiated volume.

The measurement of the positions, relative intensities and widths of the diffracted peaks were determined by complete modelling of the diffractograms using pseudo-Voigt type symmetrical analytical functions with a Gauss-Lorentz ratio fixed at 0.5. These functions are symmetrical for all peaks except for the maximum intensity peak (d=1.39 Å) the two half-widths of which are not equivalent. Further, to differentiate the doublet of peaks located at 1.99 and 1.96 Å, the two pseudo-Voigt symmetrical functions were constrained to adopt the same full width at half the maximum.

The positions, intensities and widths of the functions were refined to adjust the calculated profiles to the experimental peaks—we refined the positions, intensities and widths.

The refined parameters for the calculated peaks which qualified the experimental peaks were:
positions (interplanar spacings);
intensity;
FWHM (full width at half the maximum)

A linear diffusion background was adjusted at the same time as the peak profiles. An extremely broad and low intensity peak centred at approximately 2.5 Å, which was vital to the quality of the refinement of the experimental diagram but clearly undefined, was considered to be a diffusion background supplement.

The relative intensities recorded here are expressed as the percentage of the height of the most intense peak (d=1.39 Å) above the diffusion background.

In the case of the support of the invention, the most intense peak (d=1.39 Å) has a dissymmetry which we characterized by an "asymmetry ratio" corresponding to the ratio of the left width of the peak (in °2θ) to the right width (in °2θ).

The widths of the peaks were qualified (fine (F), normal (N), broad (B), very broad (VB)) as a function of the range of the full width at half the maximum (FWHM) of the profile calculated for each experimental peak. These widths are dependent on the apparatus and the wavelength employed. The widths expressed as 2θ are dependent on the apparatus and the wavelength used for the analysis. In contrast, the qualification of the peaks (fine (F), normal (N), broad (B), very broad (VB)) deduced from these values is valid regardless of the type of apparatus and the analysis conditions used. Relative classification of the peaks with respect to their full width at half the maximum with respect to each other is valid regardless of the type of apparatus and the analysis conditions employed.

The qualification of the peaks widths is given below:

| Peak width measured at mid height under our analysis conditions (in degrees 2θ) | Peak width qualification |
| --- | --- |
| <0.8 | Fine (F) |
| 0.8-2.0 | Normal (N) |
| 2.0-3.0 | Broad (B) |
| >3.0 | Very broad (VB) |

For the catalysts of the invention comprising palladium on an oxide of aluminium support, in the calcined state the oxide of aluminium support generally has a diffractogram obtained by X ray diffraction comprising peaks which correspond to the following interplanar spacings, relative intensities and peak widths:

| Interplanar spacings d ($10^{-10}$ m) ±5 × $10^{-3}$ d | Relative intensities $I/I_0$ (%) | Peak width |
| --- | --- | --- |
| 4.54 | 3-10 | B-VB |
| 2.70-2.75 | 5-25 | VB |
| 2.41 | 35-45 | B |
| 2.28 | 15-30 | F |
| 2.10 | 0-10 | N-VB |
| 1.987 | 30-50 | N |
| 1.958 | 30-50 | N |
| 1.642 | 0-5 | B-VB |
| 1.519 | 10-20 | VB |
| 1.394 | 100 | N |

The ratio of the intensities of peaks located at 1.987 Å and 1.958 Å $(I/I_0)_{1.987}/(I/I_0)_{1.958}$ is in the range 1.1 to 1.8, preferably in the range 1.2 to 1.7.

The asymmetry ratio of the peak located at 1.394 Å is in the range 1.35 to 2.0.

Use of Catalyst of the Invention

The catalyst of the invention may be used in processes involving the transformation of organic compounds. Thus, the catalyst of the invention may be used in processes comprising reactions for hydrogenation of compounds comprising aromatic, ketone, aldehyde, acid or nitro functions, for the hydrogenation of carbon monoxide to $C_1$-$C_6$ alcohols, to methanol or dimethyl-ether, reactions for isomerization or hydro-isomerization, hydrogenolysis, and in general reactions involving carbon-carbon bond cleavage or formation.

The operating conditions generally used for these reactions are as follows: a temperature in the range 0° C. to 500° C., preferably in the range 25° C. to 350° C., a pressure in the range 0.1 to 20 MPa, preferably in the range 0.1 to 10 MPa, an hourly space velocity (HSV) in the range 0.1 to 50 $h^{-1}$, preferably in the range 0.5 to 20 $h^{-1}$ for a liquid feed; and in the range 500 to 30000 $h^{-1}$, preferably in the range 500 to 15000 $h^{-1}$ for a gas feed. When hydrogen is present, the hydrogen/feed molar ratio is in the range 1 to 500 liters per liter, preferably in the range 10 to 250 liters per liter.

The use of the catalyst of the invention and the conditions for its use must be adapted by the user to the reaction and technology employed.

The catalyst of the invention may also be used in reactions for the hydrogenation of compounds comprising acetylenic, dienic, or olefinic functions.

The invention also concerns a process for selective hydrogenation by bringing a feed into contact with the catalyst of the invention or the catalyst prepared in accordance with the invention, said feed being selected from the group constituted by $C_3$ steam cracking cuts, $C_4$ steam cracking cuts, $C_5$ steam cracking cuts and steam cracking gasolines also termed pyrolysis gasoline.

In accordance with a preferred application, the catalysts of the invention are employed for reactions for the selective hydrogenation of polyunsaturated hydrocarbon cuts derived from steam cracking and/or catalytic cracking, preferably polyunsaturated hydrocarbon cuts derived from steam cracking.

Hydrogenation of $C_3$ to $C_5$ Cuts

Processes for the conversion of hydrocarbons such as steam cracking or catalytic cracking are operated at high temperature and produce a large variety of unsaturated molecules such as ethylene, propylene, linear butenes, isobutene, pentenes as well as unsaturated molecules containing up to approximately 15 carbon atoms.

Polyunsaturated compounds are formed at the same time: acetylene, propadiene and methylacetylene (or propyne), 1,2- and 1,3-butadiene, vinylacetylene and ethylacetylene, and other polyunsaturated compounds with a boiling point corresponding to the $C_5^+$ gasoline fraction.

All of these polyunsaturated compounds have to be eliminated to allow these various cuts to be used in petrochemical processes such as polymerization units.

Thus, for example, the $C_3$ steam cracking cut may have the following mean composition: of the order of 90% by weight propylene, of the order of 3% to 8% by weight propadiene and methylacetylene, the remainder essentially being propane. In certain $C_3$ cuts, between 0.1% and 2% by weight of $C_2$ and $C_4$ may also be present. The specifications concerning the concentrations of these polyunsaturated compounds for petrochemicals and polymerization units are very low: 20-30 ppm by weight of MAPD (methylacetylene and propadiene) for chemical quality propylene and less than 10 ppm by weight or even down to 1 ppm by weight for "polymerization" quality.

A $C_4$ steam cracking cut has the following mean molar composition, for example: 1% butane, 46.5% butene, 51% butadiene, 1.3% vinylacetylene (VAC) and 0.2% butyne. In certain $C_4$ cuts, between 0.1% and 2% by weight of $C_3$ and $C_5$ may also be present. Here again, the specifications are severe: the diolefins content is strictly less than 10 ppm by weight for a $C_4$ cut which will be used in petrochemicals or polymerization.

A $C_5$ steam cracking cut has the following mean composition by weight: 21% pentanes, 45% pentenes, 34% pentadienes.

The selective hydrogenation process is imposed progressively to eliminate polyunsaturated compounds from $C_3$ to $C_5$ oil cuts since this process allows the conversion of the most unsaturated compounds to the corresponding alkenes, avoiding total saturation and thus the formation of the corresponding alkanes.

Selective hydrogenation may be carried out in the gas or liquid phase, preferably in the liquid phase. A liquid phase reaction can reduce the energy cost and increase the cycle life of the catalysts.

For a liquid phase reaction, the pressure is generally in the range 1 to 3 MPa, the temperature in the range 2° C. to 50° C. and the hydrogen/(polyunsaturated compounds to be hydrogenated) molar ratio is in the range 0.1 to 4, preferably in the range 1 to 2.

For a gas phase hydrogenation reaction, the pressure is generally in the range 1 to 3 MPa, the temperature in the range 40° C. to 120° C. and the hydrogen/(polyunsaturated compounds to be hydrogenated) molar ratio is in the range 0.1 to 4, preferably in the range 1 to 2.

Hydrogenation of Steam Cracked Gasoline

Steam cracking principally produces ethylene, propylene, a $C_4$ cut and steam cracked gasoline also termed pyrolysis gasoline.

In accordance with another preferred mode, the feed is a pyrolysis gasoline. Pyrolysis gasoline corresponds to a cut with a boiling point which is generally in the range 0° C. to 250° C., preferably in the range 10° C. to 220° C. This feed generally comprises the $C_5$-$C_{12}$ cut with traces of $C_3$, $C_4$, $C_{13}$, $C_{14}$, $C_{15}$ (for example in the range 0.1% to 3% by weight for each of these cuts).

As an example, a $C_5$-200° C. cut generally has the following composition as a % by weight:
Paraffins: 8-12
Aromatics: 58-62
Mono-olefins: 8-10
Diolefins: 18-22
Sulphur: 20-300 ppm Selective hydrogenation of a pyrolysis gasoline consists of bringing the feed to be treated into contact with hydrogen introduced in excess into one or more reactors containing the hydrogenation catalyst.

The flow rate of the hydrogen is adjusted in order to provide a sufficient quantity to theoretically hydrogenate all of the diolefins, acetylenes and aromatic alkenyl compounds and to maintain an excess of hydrogen at the reactor outlet. In order to limit the temperature gradient in the reactor, it may be advantageous to recycle a fraction of the effluent to the inlet and/or to the centre of the reactor.

In the case of selective hydrogenation of pyrolysis gasoline, the hydrogen/(polyunsaturated compounds to be hydrogenated) molar ratio is generally in the range 1 to 2, the temperature is generally in the range 40° C. to 200° C., preferably in the range 50° C. to 180° C., the hourly space velocity (corresponding to the volume of hydrocarbon per volume of catalyst per hour) is generally in the range $0.5\ h^{-1}$ to $10\ h^{-1}$, preferably in the range $1\ h^{-1}$ to $5\ h^{-1}$ and the pressure is generally in the range 1.0 MPa to 6.5 MPa, preferably in the range 2.0 MPa to 3.5 MPa.

EXAMPLES

Example 1

Catalyst A (in Accordance with the Invention)

The support for catalyst A was prepared in accordance with the first variation of the support preparation mode. The steps for preparing the support for catalyst A in the form of beads were as follows:

s1) Dehydration by flash calcining hydrargillite in order to obtain an active alumina powder. A stream of hot gas eliminated and entrained the evaporated water very rapidly. The temperature was fixed at 800° C. and the contact time for the material to be dehydrated with the gas was 1 second. The active alumina powder obtained was ground then washed with water;

s2) Forming said active alumina powder to obtain beads with a loose packing density of 785 kg/m³ and a diameter mainly in the range 2 to 4 mm;

Forming said active alumina powder to obtain beads, termed granulation, was carried out using a rotary bowl granulator;

s3) Heat treating said beads at 720° C. to provide a specific surface area of 200 m²/g;

s4) Hydrothermal treatment of said beads by impregnating with an aqueous acid solution. The hydrothermal treatment was carried out at a temperature of 200° C. for 6.5 hours, in a rotating basket autoclave, and the impregnation solution was an aqueous acid solution comprising aluminium nitrate. These percentages were calculated by weight with respect to the mass of alumina introduced.

s5) Calcining the agglomerates obtained at a temperature of 650° C. for 2 hours. The agglomerates obtained had a specific surface area of 142 m²/g.

An aqueous solution of palladium nitrate $Pd(NO_3)_2$ was prepared at 25° C. by diluting 7.5 g of a 10% by weight aqueous palladium nitrate solution and 10% by weight nitric acid (Aldrich) in demineralized water to a volume which corresponded to the pore volume of the alumina support. This solution was then impregnated into 100 grams of prepared support. The XRD signature of the support was as follows:

| Interplanar spacings<br>d (10⁻¹⁰ m)<br>±5 × 10⁻³ d | Relative<br>intensities<br>I/I₀ (%) | Peak width |
|---|---|---|
| 4.54 | 7 | B |
| 2.74 | 20 | VB |
| 2.41 | 41 | B |
| 2.28 | 22 | F |
| 2.09 | 4 | N |
| 1.993 | 47 | N |
| 1.953 | 34 | N |
| 1.651 | 4 | B |
| 1.517 | 17 | VB |
| 1.394 | 100 | N |

Asymmetry ratio of peak at 1.394 Å: 1.63
$I_{1.99}/I_{1.95}$ intensity ratio: 1.38.

Catalyst A obtained was dried in air at 120° C., then was calcined for 2 hours at 450° C. in air. Catalyst A contained 0.3% by weight of palladium.

Example 2

Catalyst B (in Accordance with the Invention)

The support for catalyst B was prepared in accordance with the first variation of the support preparation mode. The operating conditions and the method for preparing the support were the same as those employed in Example 1.

An aqueous solution of palladium nitrate $Pd(NO_3)_2$ was prepared at 25° C. by diluting 7.5 g of a 10% by weight aqueous palladium nitrate solution and 10% by weight nitric acid (Aldrich) in demineralized water to a volume which corresponded to the pore volume of the alumina support less the volume of sodium hydroxide which was then added. Next, 9.9 ml of a 1M solution of sodium hydroxide (Aldrich) was added dropwise, with stirring. This solution was then impregnated into 100 grams of prepared support. The XRD signature of the support was as follows:

| Interplanar spacings<br>d (10⁻¹⁰ m)<br>±5 × 10⁻³ d | Relative<br>intensities<br>I/I₀ (%) | Peak width |
|---|---|---|
| 4.53 | 6 | VB |
| 2.71 | 23 | VB |
| 2.41 | 39 | B |
| 2.28 | 25 | F |
| 2.10 | 6 | B |
| 1.993 | 51 | N |
| 1.952 | 40 | N |
| 1.647 | 4 | B |
| 1.522 | 16 | VB |
| 1.393 | 100 | N |

Asymmetry ratio of peak at 1.394 Å: 1.70
$I_{1.99}/I_{1.95}$ intensity ratio: 1.28.

Catalyst B obtained was dried in air at 120° C., then was calcined for 2 hours at 450° C. in air. Catalyst B contained 0.3% by weight of palladium.

Example 3

Catalyst C (not in Accordance with the Invention)

The support for catalyst C was prepared in accordance with the first variation of the support preparation mode. The operating conditions and the method for preparing the support were the same as those employed in Example 1 apart from the fact that the calcining of step s5) was carried out at 950° C. for 2 hours. It produced agglomerates with a specific surface area of 67 m²/g.

An aqueous solution of palladium nitrate $Pd(NO_3)_2$ was prepared at 25° C. by diluting 7.5 g of a 10% by weight aqueous palladium nitrate solution and 10% by weight nitric acid (Aldrich) in demineralized water to a volume which corresponded to the pore volume of the alumina support. This solution was then impregnated into 100 grams of prepared support. The XRD signature of the support was as follows:

| Interplanar spacings<br>d (10⁻¹⁰ m)<br>±5 × 10⁻³ d | Relative<br>intensities<br>I/I₀ (%) | Peak width |
|---|---|---|
| 5.18 | 4 | N-B |
| 4.58 | 7 | N |
| 4.09 | 2 | N |
| 2.82 | 17 | N |
| 2.73 | 36 | F |
| 2.44 | 34 | N |
| 2.29 | 33 | N |
| 1.997 | 77 | N |
| 1.942 | 39 | N |
| 1.796 | 7 | N |
| 1.539 | 8 | N |
| 1.511 | 8 | N |
| 1.391 | 100 | N |

Asymmetry ratio of peak at 1.394 Å: 2.54
$I_{1.99}/I_{1.95}$ intensity ratio: 1.97.

Catalyst C obtained was dried in air at 120° C., then was calcined for 2 hours at 450° C. in air. Catalyst C contained 0.3% by weight of palladium.

Example 4

Catalyst D (not in Accordance with the Invention)

The support for catalyst D was prepared in accordance with the first variation of the support preparation mode. The operating conditions and the method for preparing the support were the same as those employed in Example 1 apart from the fact that the calcining of step s5) was carried out at 950° C. for 2 hours. It produced agglomerates with a specific surface area of 67 m²/g.

An aqueous solution of palladium nitrate $Pd(NO_3)_2$ was prepared at 25° C. by diluting 7.5 g of a 10% by weight aqueous palladium nitrate solution and 10% by weight nitric acid (Aldrich) in demineralized water to a volume which corresponded to the pore volume of the alumina support less the volume of sodium hydroxide added subsequently. Next, 9.9 ml of a 1M sodium hydroxide solution (Aldrich) was added dropwise with stirring. This solution was then impregnated into 100 grams of prepared support. The XRD signature of the support was as follows:

| Interplanar spacings<br>d (10⁻¹⁰ m)<br>±5 × 10⁻³ d | Relative<br>intensities<br>I/I₀ (%) | Peak width |
|---|---|---|
| 5.18 | 3 | N-B |
| 4.58 | 4 | B |
| 4.09 | 1 | N |
| 2.81 | 14 | B |
| 2.73 | 17 | F |
| 2.43 | 35 | B |
| 2.29 | 31 | N |

-continued

| Interplanar spacings d ($10^{-10}$ m) ±5 × $10^{-3}$ d | Relative intensities $I/I_0$ (%) | Peak width |
|---|---|---|
| 1.994 | 73 | N |
| 1.948 | 38 | N |
| 1.787 | 5 | B |
| 1.535 | 6 | N |
| 1.510 | 6 | N |
| 1.391 | 100 | N |

Asymmetry ratio of peak at 1.394 Å: 2.78
$I_{1.99}/I_{1.95}$ intensity ratio: 1.92.

Catalyst D obtained was dried in air at 120° C., then was calcined for 2 hours at 450° C. in air. Catalyst D contained 0.3% by weight of palladium.

Example 5

Catalytic Test for Hydrogenation of a Styrene-Isoprene Mixture in the Presence of S Before the catalytic test, catalysts A, B, C and D were treated in a stream of 1 liter of hydrogen per hour per gram of catalyst with a temperature ramp-up of 300° C./h and a constant temperature stage at 150° C. of 2 hours.

The catalysts then underwent a hydrogenation test in a perfectly stirred "Grignard" type batch reactor. To this end, 4 ml of reduced catalyst beads were fixed in the absence of air in an annular basket located around a stirring arm. The baskets used in the reactors were of the Robinson Mahonnay type.

Hydrogenation was carried out in the liquid phase.

The composition of the feed was as follows: 8% by weight styrene, 8% by weight isoprene, 10 ppm of S introduced in the form of pentanethiol, 100 ppm of S introduced in the form of thiophene, the solvent being n-heptane.

The test was carried out at a constant pressure of 3.5 MPa of hydrogen and at a temperature of 45° C. The reaction products were analyzed by gas chromatography.

The catalytic activities were expressed in moles of $H_2$ consumed per minute and per gram of palladium and are reported in Table 1.

TABLE 1

Activities measured for the hydrogenation of a styrene-isoprene mixture in the presence of sulphur.

| Catalyst | Activity* |
|---|---|
| Catalyst A (in accordance) | 0.42 |
| Catalyst B (in accordance) | 0.51 |
| Catalyst C (not in accordance) | 0.36 |
| Catalyst D (not in accordance) | 0.44 |

*in (moles $H_2$)/[min × (grams of palladium)]

Catalyst A in accordance with the invention was approximately 17% more active than catalyst C, not in accordance with the invention, for an identical impregnation step. Catalyst B in accordance with the invention was approximately 16% more active than catalyst D, not in accordance with the invention, for an identical impregnation step.

The preceding examples can be repeated with similar success by substituting the generically or specifically described reactants and/or operating conditions of this invention for those used in the preceding examples.

In the foregoing and in the examples, all temperatures are set forth uncorrected in degrees Celsius and, all parts and percentages are by weight, unless otherwise indicated.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding French application No. 08/03.482, filed Jun. 20, 2008 are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A catalyst comprising palladium on an oxide of aluminium support, the oxide of aluminium support having, in the calcined state, a diffractogram obtained by X ray diffraction comprising peaks which correspond to the following interplanar spacings, d, and relative intensities, $I/I_0$:

| Interplanar spacings d ($10^{-10}$ m) ±5 × $10^{-3}$ d | Relative intensities $I/I_0$ (%) |
|---|---|
| 4.54 | 3-10 |
| 2.70-2.75 | 5-25 |
| 2.41 | 35-45 |
| 2.28 | 15-30 |
| 2.10 | 0-10 |
| 1.987 | 30-50 |
| 1.958 | 30-50 |
| 1.642 | 0-5 |
| 1.519 | 10-20 |
| 1.394 | 100. |

2. A catalyst according to claim 1, in which the oxide of aluminium support has, in the calcined state, a diffractogram comprising peaks which correspond to the following interplanar spacings and relative intensities:

| Interplanar spacings d ($10^{-10}$ m) ±5 × $10^{-3}$ d | Relative intensities $I/I_0$ (%) | Peak width |
|---|---|---|
| 4.54 | 3-10 | B-VB |
| 2.70-2.75 | 5-25 | VB |
| 2.41 | 35-45 | B |
| 2.28 | 15-30 | F |
| 2.10 | 0-10 | N-VB |
| 1.987 | 30-50 | N |
| 1.958 | 30-50 | N |
| 1.642 | 0-5 | B-VB |
| 1.519 | 10-20 | VB |
| 1.394 | 100 | N. |

3. A catalyst according to claim 2, in which the palladium content in the catalyst is in the range of 0.01% to 2% by weight and the specific surface area of the support is in the range of 60 to 210 m²/g.

4. A catalyst according to claim 3, in which the diffractogram of the catalyst comprises, in addition to the characteristic peaks of the support, the characteristic peaks of palladium in the oxide form at interplanar spacings d (expressed in $10^{-10}$ m) of: 2.67, 2.65, 2.15, 1.676, 1.535, 1.523.

5. A catalyst according to claim 2, in which the diffractogram of the catalyst comprises, in addition to the characteristic peaks of the support, the characteristic peaks of palladium in the reduced form at interplanar spacings d (expressed in $10^{-10}$ m) of: 2.25, 1.945, 1.375.

6. A catalyst according to claim 5, in which the ratio of the relative intensities at respective interplanar spacings of $1.987 \times 10^{-10}$ m and $1.958 \times 10^{-10}$ m is such that $(I/I_0)_{1.987}/(I/I_0)_{1.958}$ is in the range of 1.1 to 1.8.

7. A catalyst according to claim 6, having an asymmetry ratio of the peak located at $1.394 \times 10^{-10}$ m in the range of 1.35 to 2.0.

8. A catalyst according to claim 1, in which the palladium content in the catalyst is in the range 0.01% to 2% by weight and the specific surface area of the support is in the range 60 to 210 $m^2$/g.

9. A catalyst according to claim 1, in which the diffractogram of the catalyst comprises, in addition to the characteristic peaks of the support, the characteristic peaks of palladium in the oxide form at interplanar spacings d (expressed in $10^{-10}$ m) of: 2.67, 2.65, 2.15, 1.676, 1.535, 1.523.

10. A catalyst according to claim 1, in which the diffractogram of the catalyst comprises, in addition to the characteristic peaks of the support, the characteristic peaks of palladium in the reduced form at interplanar spacings d (expressed in $10^{-10}$ m) of: 2.25, 1.945, 1.375.

11. A catalyst according to claim 1, in which the ratio of the relative intensities at respective interplanar spacings of $1.987 \times 10^{-10}$ m and $1.958 \times 10^{-10}$ m is such that $(I/I_0)_{1.987}/(I/I_0)_{1.958}$ is in the range 1.1 to 1.8.

12. A catalyst according to claim 1, in which the asymmetry ratio of the peak located at $1.394 \times 10^{-10}$ m in the range 1.35 to 2.0.

13. In a process for selective catalytic hydrogenation, in which the catalyst is brought into contact with a feed selected from the group constituted by steam cracking $C_3$ cuts, steam cracking $C_4$ cuts, steam cracking $C_5$ cuts and steam cracked gasoline, the improvement wherein the catalyst is according to claim 1.

* * * * *